United States Patent
Huang et al.

(10) Patent No.: US 6,375,818 B1
(45) Date of Patent: Apr. 23, 2002

(54) SURFACES WITH REDUCED ELECTROOSMOTIC FLOW

(75) Inventors: Tung-Liang Huang, Placentia; M. Parameswara Reddy, Brea, both of CA (US)

(73) Assignee: Beckman Coulter, Inc., Fullerton, CA (US)

(*) Notice: Subject to any disclaimer, the term of this patent is extended or adjusted under 35 U.S.C. 154(b) by 0 days.

(21) Appl. No.: 09/328,009

(22) Filed: Jun. 8, 1999

(51) Int. Cl.$^7$ ................................................. G02N 27/26
(52) U.S. Cl. ........................ 204/454; 204/601; 427/235; 427/238; 428/34.7
(58) Field of Search ................................. 427/2.11, 230, 427/235, 238; 204/454, 600, 601; 428/34.4, 34.7

(56) References Cited

U.S. PATENT DOCUMENTS

| | | | |
|---|---|---|---|
| 5,552,028 A | 9/1996 | Madabhushi et al. | 204/451 |
| 5,567,292 A | 10/1996 | Madabhushi et al. | 204/451 |
| 5,605,613 A | 2/1997 | Shieh | 204/451 |
| 5,792,331 A | 8/1998 | Srinivasan et al. | 204/454 |
| 5,840,388 A | 11/1998 | Karger et al. | 428/36.91 |
| 5,948,227 A * | 9/1999 | Dubrow | 204/455 |

FOREIGN PATENT DOCUMENTS

| EP | 0321736 A2 * | 6/1989 | G01N/33/53 |
|---|---|---|---|
| EP | 0708329 A2 * | 9/1995 | G01N/27/447 |

OTHER PUBLICATIONS

Yao et al. "Manipulation of electroosmotic flow in capillary electrophoresis", Journal of Chromatography, 636 (1993) 21–29.*

Gilges et al., "Capillary Zone Electrophoresis Separations of Basic and Acidic Proteins Using Poly(vinyl alcohol) Coatings in Fused Silica Capillaries," Anal. Chem., 66, No. 13, pp. 2038–2046 (Jul. 1, 1994).

Freemantle, Michael, "Downsizing Chemistry," Chemical and Engineering News, pp. 27–36 (Feb. 22, 1999).

Jorgenson et al, "Capillary Zone electrophoresis", Science, vol. 222, pp. 266–272 (Oct. 21, 1983).

Lauer, et al, "Capillary Zone electrophoresis of Proteins in Untreated Fused Silica Tubing", Anal. Chem., vol. 58, No. 1, pp. 166–170, (1986).

* cited by examiner

Primary Examiner—Jill Warden
Assistant Examiner—Alex Noguerola
(74) Attorney, Agent, or Firm—William H. May; Arnold Grant

(57) ABSTRACT

An article of manufacture is provided that is useful in differentiating between solutes, such as during electrophoretic separations. An embodiment of the article is a capillary tube, that carries a polymer along the inner wall of the capillary tube. The polymer is effective to reduce undesired interactions and preferably includes a polylactam that is absorbed to the surface before the surface is exposed to the solutes. A preferred polylactam is poly(vinylpyrrolidone) with a molecular weight greater than about 1,000,000 daltons (weight-average).

23 Claims, 1 Drawing Sheet

SURFACES WITH REDUCED ELECTROOSMOTIC FLOW

FIELD OF THE INVENTION

The present invention generally relates to solid surfaces that are usefully exposed to flowing solute, and particularly to articles such as capillaries or microchips that have a polymer adsorbed to their surfaces which is effective to reduce electroosmotic flow when the articles are used in electrophoretic separations.

BACKGROUND OF THE INVENTION

Electrophoresis is a well-known technique for the separation of charged species by utilizing their differences in rate of migration under the influence of an electrical field. The advantages associated with capillary electrophoresis are numerous. Quantitative information can be achieved with very small sample sizes, and the amount of gel or buffer consumed is minuscule. Capillary electrophoresis is associated with certain phenomenon which are not present in traditional slab gel electrophoresis. One of these is the now familiar electroosmotic flow phenomenon characterized by bulk flow of buffer solutions toward one of the electrodes.

For many electrophoretic applications, electroosmotic flow is undesirable and eliminating or substantially reducing the bulk flow is preferred. Generally, when electroosmotic flow is reduced to a minimum, electrophoretic sample components move only by electrophoretic migration, which improves analysis reproducibility and mass recovery of sample components.

Jorgenson and Lukacs had noted that separation of model proteins, such as cytochrome, lysozyme, and ribonuclease A, in untreated fused silica capillaries with a phosphate buffer at pH 7 was accompanied by strong tailing, and suggested this might be caused by Coulombic interactions of the positively charged proteins and the negatively charged capillary wall. (Jorgenson et al., *Science*, 222, 1983, pp. 266–272.) The authors reported investigating Teflon capillaries, but found these also exhibit significant adsorptivity toward proteins. They attempted to deactivate the surface of fused silica with groups such as trimethyl silane, octadecylsilane, aminopropylsilane, and cross-linked methyl cellulose, which apparently did not work. They then turned to bonding glycol-containing groups to the surface.

Lauer and McManigill, *Analytical Chemistry*, 58, 1986, p. 166, reported that the Coulombic repulsion between proteins and the capillary wall of silica capillaries can overcome adsorption tendencies of the proteins with the capillary wall. They demonstrated separations of model proteins (ranging in molecular weight from 13,000 to 77,000) by varying the solution pH relative to the isoelectric point (pI) of the proteins to change their net charge. However, disadvantages of this approach are that silica begins to dissolve above pH 7, which shortens column life and degrades performance, and only proteins with pI's less than the buffer pH can be analyzed.

Yet another approach to the problem of undesirable protein interactions with the capillary wall is described by U.S. Pat. No. 4,680,201, inventor Hjerten, issued Jul. 14, 1987, wherein a method for preparing a thin-wall, narrow-bore capillary tube for electrophoretic separations is provided by use of a bifunctional compound in which one group reacts specifically with the glass wall and other with a monomer taking part in a polymerization process. This free-radical procedure results in a polymer coating, such as polyacrylamide coating, and is suggested for use in coating other polymers, such as poly(vinylalcohol) and poly (vinylpyrrolidone).

Other covalently bound species have subsequently been described. U.S. Pat. No. 5,605,613, issued Feb. 25, 1997, inventor Shieh, discloses capillary columns having a neutral cross-linked hydrophilic coating on the interior wall surfaces, which is said to reduce analyte interaction with the interior surface. The coated column includes a polymer covalently bound to the interior surface.

U.S. Pat. No. 5,840,388, issued Nov. 24, 1998, inventors Karger et al., describes a coated microcapillary column for high performance electrophoresis in which a polymeric coating layer is formed by polymerizing an organic compound such as polyvinyl alcohol to the column surface. U.S. Pat. No. 5,792,331, issued Aug. 11, 1998, inventors Srinivasan et al., discloses a method of coating a capillary or chromatography packing by covalently bonding a polymer such as poly(vinylpyrrolidone) ("PVP") to capillary walls.

Although capillary treatments involving chemical bonding (that is, covalent bonding) can function to reduce electroosmotic flow, the treatment processes are relatively time consuming and expensive, and also tend to create relatively thick coatings on the interiors of the capillary columns. Capillary columns used in capillary electrophoresis typically are fabricated of lengths of silica tubing having an inner diameter on the order of 25 $\mu$m to 200 $\mu$m, and thus the covalently bonded coatings can significantly increase the time for achieving electrophoretic separations.

U.S. Pat. No. 5,552,028, issued Sep. 3, 1996, inventors Madabhushi et al., discloses a composition for separating polynucleotides in which one component of the separation medium includes a silica-adsorbing polymer; and, U.S. Pat. No. 5,567,292, issued Oct. 22, 1996, inventors Madabhushi et al., discloses a method of suppressing electroosmotic flow by which a separation medium is provided that contains a silica-adsorbing polymer in a concentration of the separation medium in a range between about 0.001% and about 10% wt./v. These two Madabhushi et al. patents thus disclose a type of dynamic coating methods, whereby the eluent, or separation medium, itself contains additives for coating during the separations so as to mask surface charges; however, these additives may interact with the analytes which can lead to some unexpected and undesired results, and optimization tends to be limited to the use of certain specific separation matrices.

SUMMARY OF THE INVENTION

It is an object of the present invention to provide solid surfaces, such as capillary tubes that are useful for electrophoretic separations, where interactions between solutes flowed along the surfaces are considerably reduced, while preparation of the inventive surfaces is simple, fast, relatively inexpensive yet results in long-term stability.

Further objects and advantages of the invention will become apparent to those skilled in the art upon examination of the specification and appended claims, as well as in practice of the present invention.

In one aspect of the present invention, an article of manufacture is provided that is useful in differentiating between solutes, such as when the article is exposed to a flow of solutes during electrophoretic separations where the solutes include charged species such as proteins and oligonucleotides. Particularly preferred articles of the invention are formed as capillary tubes and are useful in DNA sequencing analysis, DNA fragment analysis and sizing, and protein separation and analysis. The inventive articles have a solid surface that carries a polymer. The polymer is adsorbed to the surface and functions to reduce interactions with the surface. The adsorbed polymer preferably is a polylactam, most preferably is poly(vinylpyrrolidone), or PVP, and preferably with a molecular weight of greater than about 1,000,000 daltons (weight-average) which has been simply and quickly coated by adsorption onto the inner wall of capillaries prior to introduction of the separation medium.

Surfaces treated in accordance with the invention have reduced electroosmotic flow, and may be used in virtually any capillary electrophoretic separation, where it is desirable to minimize or eliminate electroosmotic flow. The inventive surfaces are particularly useful as coated capillary columns in electrophoretic separation systems such as the CEQ2000, P/ACE MDQ, and Paragon CZE 1000 systems manufactured and sold by Beckman Coulter, Inc., Fullerton, Calif. for applications such as in DNA sequencing analysis, DNA fragment analysis and sizing, and protein separation and analysis.

DETAILED DESCRIPTION OF THE PREFERRED EMBODIMENTS

Figure 1:
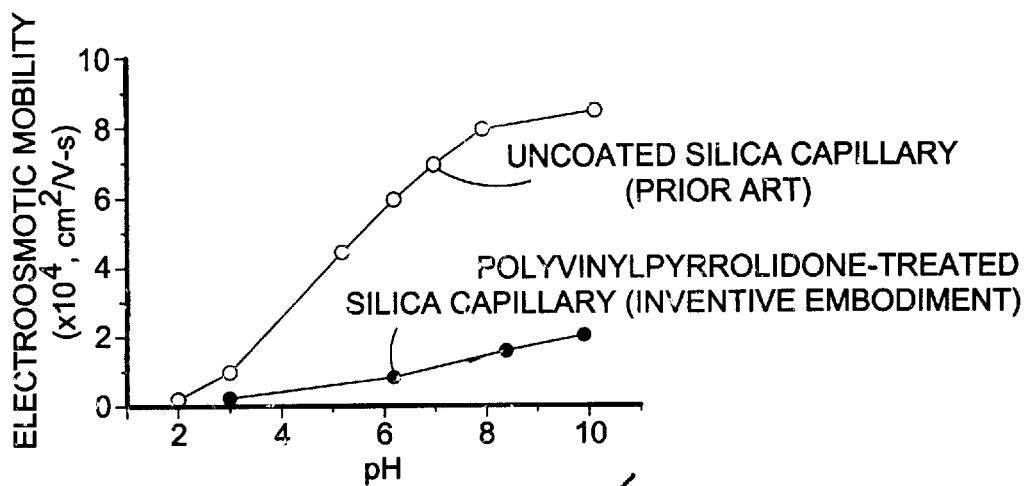
FIG. 1 compares electroosmotic flow for an uncoated (prior art) capillary with an inventive embodiment where pH is plotted against electroosmotic flow.

In one form of preferred embodiments of the present invention, capillary tubings fabricated of fused silica are treated by adsorbing a polymer, preferably a polylactam, onto the interior bore. Depending upon the particular analytical application, the tubings to be treated can vary in length and diameter. Articles fabricated of materials other than silica are believed to be suitably treated in accordance with this invention.

In another form of preferred inventive embodiments, microchannels defined by or carried on miniaturized apparatus such as microchips are treated by adsorbing a polymer onto the channels. Microchips are useful in microanalytical systems. For example, in a Feb. 22, 1999, Chemical & Engineering News article, typical microchips used for miniaturized chemical systems were described where a 2 or 3 cm square of silicon, glass, quartz, or plastic is etched or molded with chambers and channels having cross sections as low as 50 $\mu$m. The miniaturized components are useful with chromatography and electrophoresis separation columns, polymerized chain reaction vessels, pumps, and valves and the like—all for use on cm-sized microchips.

A column, such as a tubing or a miniaturized channel, can be from about 5 cm to 2000 cm in length and be from about 5 $\mu$m to about 200 $\mu$m in inner diameter (width if using a channel), although as noted in the miniaturized apparatus, the chips are more typically about 2 or 3 cm$^2$.

Although capillary columns and microchannels on microchips useful for electrophoretic separation of components in a sample, particularly components such as biomolecules (e.g. proteins and oligonucleotides), are particularly preferred embodiments, other articles that in use are exposed to flows of solutes for differentiation can be coated in accordance with this invention, such as, for example, beads and other chromatography packing materials.

Apparatus for carrying out capillary electrophoresis is well-known, and particularly contemplated uses of the inventively coated capillary columns are in electrophoretic separation systems such as the CEQ2000, P/ACE MDQ, and Paragon CZE 1000 systems manufactured and sold by Beckman Coulter, Inc., Fullerton, Calif. for applications such as in DNA sequencing analysis, DNA fragment analysis and sizing, and protein separation and analysis.

In accordance with the invention, a polymer that is effective to reduce interactions between the surface, or an interior surface such as a bore where the article is a capillary, is adsorbed to the surface. Polymers in accordance with this invention preferably are polylactams that are adsorbed to the surface prior to the surface being exposed to the sample intended to be flowed past the surface (e.g. through the column) so as to achieve electrophoretic separation of components in the sample. Suitable polylactams include PVP, and substituted PVP (such as having substituents on the ring). In particular, the polymer adsorbed onto the article preferably consists essentially of poly(vinylpyrrolidone), or "PVP," with a molecular weight (weight-average) of greater than about 1,000,000 daltons, more preferably about 1,300, 000. The upper range can vary considerably. As a practical matter, one will usually use polymers with a molecular range between 1,300,000 and 4,000,000 daltons.

The silica-adsorbing quality of polymers can be measured in a number of well-known ways, such as by ellipsometry, determining changes in the hydrodynamic properties of adsorbent test particles, determination of adsorption isotherms, or like methods. Such techniques are described in Malmsten et al., *Macromolecules*, 25, pp. 2474–2481 (1992); Rob and Smith, *European Polymer J.*, 10, pp. 1005–1010 (1974); Vincent et al, *Surf. Colloid Sci.*, 12, pp. 1–117 (1982); Takahashi et al., *Advances in Polymers Science*, 46, pp. 1–65 (1982), and like references. The degree of adsorption may also be measured indirectly by observing the reduction of electroendoosmotic flow under a set of standard values.

For polynucleotide separations, the adsorbed polylactam is preferably characterized by the relationship between resolving power and polynucleotide length for a selected "ladder" of polynucleotides under a standard set of conditions. Resolving power is conveniently expressed in terms of the number of theoretical plates, N, of the test system: $N=(L/\Delta)^2$, where L is the average path length of a test analyte under a peak from injection port to detector (usually position of peak maximum) and $\Delta$ is the variance of the peak.

Exemplary ladders of different-sized polynucleotides in the above-mentioned size ranges are available in commercially available kits, e.g., the 100 basepair double stranded DNA ladder from BRL-GIBCO, the Taq DNA Sequencing Standard from Applied Biosystems, Inc., CEQ DNA test sample from Beckman Coulter, Inc., or the like.

We have found that articles of the invention having adsorbed polylactams are preferably stored until ready for use in a storage gel. The particularly preferred storage gel uses linear polyacrylamide as the gelling component (although other gels used as storage gels are certainly feasible) and may be prepared by dissolving 3% (w/v) of polyacrylamide, particularly with a weight-average molecular weight of 2,000,000 to 10,000,000, in a buffer consisted of 100 mM Taps, 20 mM Tris, and 1 mM EDTA. Before use, the storage gel may or may not be removed, as the particular application warrants. The pH of the gel is about 7.8. The polylactam, such as the preferred PVP, is preferably dissolved in a buffer (we call a "reconstitution buffer"). This preferred reconstitution buffer may be prepared from 100 mM taps, 20 mM Tris, 7 M urea, and 1 mM EDTA. The pH of the buffer is about 8.2.

Broadly, polylactam treating solutions are prepared by dissolving the selected polymer (preferably in a range of 12–20% w/v) in a suitable gel buffer. The resulting polymer solution is then pumped into the capillaries to be treated, allowed to stay inside a capillary for a sufficient time, typically at least about two hours, more preferably 12 hours or overnight, and then replaced with either a suitable storage gel or the particular gel used in the capillary electrophoresis system. The viscosity values of the treating polymer solutions tend to be relatively high since the molecular weight of the preferred useful polymers are at or greater than about 1,000,000.

In making articles of the invention, such as capillary embodiments, we believe it preferable to push out unadsorbed PVP after the exposure step with a gel having a fairly high viscosity, such as the linear polyacrylamide described as the storage gel. The push out process may be performed by mechanically replacing the unadsorbed PVP with polyacrylamide gel. This "pushing out" is a preferred mode of practicing the invention, and seems to provide better coatings.

Example 1 describes preparation of a particularly preferred embodiment.

EXAMPLE 1

Pre-cut uncoated fused silica capillaries were filled with a PVP coating solution by pushing the solution through the capillaries for about 5 minutes using a mechanical pump. A PVP coating solution was prepared as follows.

A PVP polymer with a molecular weight of 1,300,000 in a concentration of 20% (w/v) and having a viscosity of 3,240 cP at 25° C. was prepared by dissolving in reconstitution buffer and was pumped through the capillaries for 5 minutes, and then allowed to stay within the capillaries for about 16 hours at room temperature 20–25° C. The coating solution was clear, which indicates full dissolution.

The particularly preferred storage gel as above described was then used to replace (push out) the PVP coating solution. This storage gel in turn was pumped out and replaced by the separation matrix prior to use. (The separation matrix was that solution used to separate the DNA fragments.)

EXAMPLE 2

A run-to-run stability test of the inventively treated capillaries was performed using the CEQ2000 DNA Sequencer. The separation conditions were 8.2 kV at 40° C. for 105 minutes, with a 50 cm separation length (52.8 cm total length). The sample was DNA sequencing fragments generated using a pUC-18 template and cyanine dye-labeled dideoxynucleotide terminators.

TABLE 1

| Run No. | Capillary Embodiment | 98% Base calling accuracy cutoff | Migration time of 328 bases (min) | Total base calling errors for up to 500 bases |
|---|---|---|---|---|
| 1 | 1 | 561 | 70.4 | 1 |
| 1 | 2 | 564 | 69.9 | 1 |
| 50 | 1 | 574 | 69 | 1 |

TABLE 1-continued

| Run No. | Capillary Embodiment | 98% Base calling accuracy cutoff | Migration time of 328 bases (min) | Total base calling errors for up to 500 bases |
|---|---|---|---|---|
| 50 | 2 | 577 | 68.7 | 3 |
| 100 | 1 | 526 | 72.3 | 0 |
| 100 | 2 | 533 | 71 | 0 |
| 150 | 1 | 526 | 71.1 | 0 |
| 150 | 2 | 547 | 79.6 | 2 |
| 200 | 1 | 550 | 68.2 | 2 |
| 200 | 2 | 575 | 66.9 | 3 |

Capillary embodiments 1 and 2 were both prepared in a manner analogous to Example 1. As indicated by the data, both capillaries showed good coating stability and separation speed.

EXAMPLE 3

The data of FIG. 1 shows the plot of pH versus electroosmotic flow in an uncoated capillary and then for an inventive embodiment prepared in a manner analogous to Example 1. The measurement of electroosmotic flow was performed by filling the capillaries with aqueous solutions having different pHs. As shown by FIG. 1, the inventively treated capillaries significantly reduced the electroosmotic flow.

The experiments were performed on a p/ACE 2200 capillary electrophoresis system (Beckman Coulter, Inc., Fullerton, Calif.). The capillary dimensions were 26 cm total length, 20 cm separation length, 100 μm inner diameter, and 200 μm outer diameter. The electroosmotic flow (EOF) marker, 1% (v/v) DMSO in water, was electrokinetically injected into the capillary at 2 kV for 10 sec, and was subjected to 8.1 kV for EOF measurements. The marker was detected at 214 nm using on-line UV detector.

EXAMPLE 4

Figure 2A:
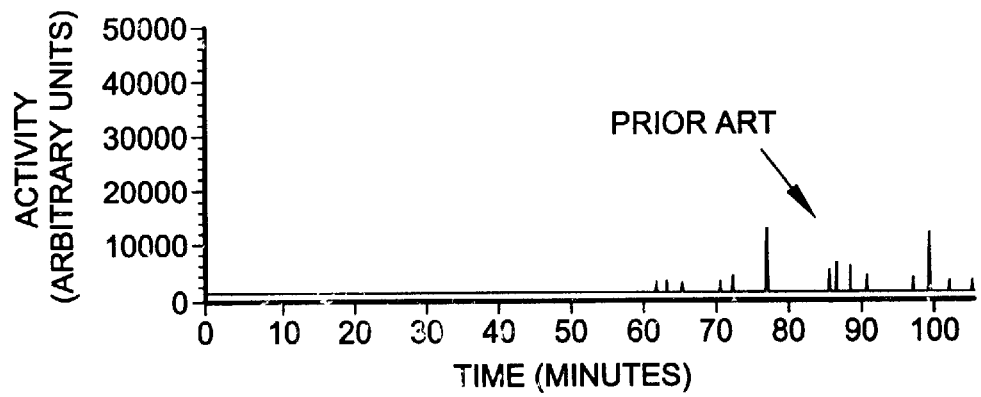
FIG. 2A illustrates an uncoated (prior art) capillary when used for DNA separation.
Figure 2B:
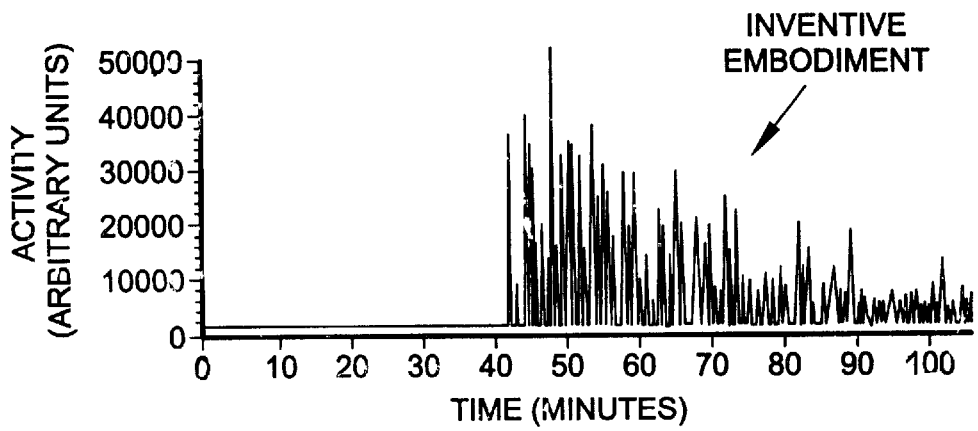
FIG. 2B is an electropherogram of a DNA sequencing separation using an inventive embodiment.

As shown in FIG. 2A, when an uncoated capillary is used for DNA separation with the Beckman Coulter CEQ2000 DNA Sequencer, there is no DNA peak observed since the strong electroosmotic flow in the uncoated capillary hampers DNA molecules from entering the capillary. However, turning to FIG. 2B, when an inventively treated embodiment (prepared in a manner analogous to Example 1) was used, there was a significant detection signal observed with the DNA sequencing fragments. The separation conditions were 8.2 kV at 40° C. for 105 minutes with a 53.5 cm separation length (56.3 cm total length). The sample was of DNA sequencing fragments generated using a pUC-18 template and cyanine dye-labeled didioxynucleotide terminators.

EXAMPLE 5

Inventively coated capillaries of the invention have been shown to demonstrate long-term stability of up to at least 400 hours at pH 8.2, as exemplified by uses in DNA sequencing separations for up to 200 runs, with a separation time of two hours for each run. Table 2 gives stability data.

TABLE 2

Long-term Stability Study of PVP-coated Capillary Array for DNA Sequencing Separation of Dye-labeled pUC18 Fragments on CEQ 2000[1]

| Array # | Run # | Percentage of runs passing the criteria of base calling accuracy at 500 bases[2,3] |
|---|---|---|
| 1 | 376 | 97.6% |
| 2 | 336 | 99.5% |
| 3 | 192 | 99.5% |

[1]The separation time was 104 minutes. Including data analysis, gel filling, and optical alignment, the total cycle time for one run was two hours.
[2]The specification for capillary stability is ≦ 95% of runs passing the criteria of base calling accuracy at 500 bases.
[3]The criteria for base calling accuracy at 500 bases is ≦ 98%.

EXAMPLE 6

During manufacture of inventive embodiments, if desired, the articles can be reconstituted as is exemplified by the following experiment. A coated capillary was first rinsed with DMSO for two hours and then with DI water for one hour to strip off the coating. The electroosmotic flow of the striped-off capillary was tested, and the results indicated that the capillary behaved like an uncoated capillary. The capillary was then re-coated with the PVP solution as earlier described. The re-coated capillary was tested with electroosmotic flow measurement and DNA separations. Both results indicated that the re-coated capillary behaved identically to a newly coated capillary.

This ability to recoat, or reconstitute, articles in accordance with the invention is particularly advantageous when the articles would be relatively expensive to replace. For example, in the miniaturized apparatus to which reference was earlier made, the microchips may include additional functions such as integrated circuits and the like. Their microchannels (that is, the coating) can be reconstituted, when desired, in accordance with this invention at a considerable savings of cost with respect to replacement of the entire apparatus.

It is to be understood that while the invention has been described above in conjunction with preferred specific embodiments, the description and examples are intended to illustrate and not limit the scope of the invention, which is defined by the scope of the appended claims.

What is claimed is:

1. A method for reducing electroosmosis during capillary separation of solutes, comprising:
   (a) providing a capillary having an interior bore extending therethrough;
   (b) adsorbing poly(vinylpyrrolidone) onto the bore by exposing the bore to a composition having at least about 12% w/v of poly(vinylpyrrolidone), wherein the poly(vinylpyrrolidone) has a molecular weight of at least about 1,000,000 daltons (weight-average); and
   (c) flowing solutes through the capillary.

2. The method of claim 1, wherein the solutes include biomolecules.

3. The method of claim 2, wherein the solutes include polynucleotides.

4. The method of claim 1, wherein the exposing is for greater than about two hours.

5. A method for reducing electroosmosis during capillary separation of solutes, comprising:
   (a) providing a capillary having an interior bore extending therethrough;
   (b) adsorbing poly(vinylpyrrolidone) onto the bore by exposing the bore to a composition having at least about 20% w/v of poly(vinylpyrrolidone), wherein the composition has a viscosity of greater than about 3000 cP at 25° C.; and
   (c) flowing solutes through the capillary.

6. The method of claim 5, wherein the solutes include biomolecules.

7. The method of claim 6, wherein the solutes include polynucleotides.

8. The method of claim 5, wherein the exposing is for greater than about two hours.

9. A method of making a capillary column useful in electrophoresis, comprising:
   providing a capillary having an interior bore extending therethrough;
   filling the bore with a poly(vinylpyrrolidone) composition containing at least about 12% w/v poly(vinylpyrrolidone);
   adsorbing poly(vinylpyrrolidone) from the composition onto the bore for a sufficient time to reduce electroosmotic flow during subsequent use of the capillary in electrophoresis; and,
   removing the poly(vinylpyrrolidone) composition while leaving adsorbed poly(vinylpyrrolidone).

10. The method of claim 9, wherein the poly(vinylpyrrolidone) has a molecular weight of at least about 1,000,000 daltons (weight-average).

11. The method of claim 9, wherein the adsorbing is by exposing the bore to the poly(vinylpyrrolidone) composition for at least about two hours.

12. The method of claim 9, wherein the removing of the poly(vinylpyrrolidone) composition includes pushing it out and replacing it with a linear polyacrylamnide.

13. The method of claim 9, wherein the poly(vinylpyrrolidone) is a substituted poly(vinylpyrrolidone).

14. The method of claim 9, wherein the capillary is made of silica.

15. The method of claim 9, wherein the poly vinylpyrrolidone) composition has a concentration of about 20% (w/v) with a viscosity of greater than about 3,000 cP at 25 ° C.

16. A capillary for separating solutes by capillary electropboresis, the capillary prepared in accordance with a method, comprising the steps of:
   (a) providing a capillary having an interior bore extending therethrough;
   (b) filling the bore with a composition comprising polyactam;
   (c) adsorbing polyactam from the composition onto the bore, wherein the adsorbed amount of polyactam is sufficient to reduce electroosmotic flow during the subsequent use of the capillary in electrophoresis; and
   (d) removing the polyactam composition from the bore while leaving the adsorbed polyactam.

17. The method of claim 16, wherein polyactam is poly(vinylpyrrolidone).

18. The method of claim 17, wherein the composition comprises at least about 12% w/v poly(vinylpyrrolidone).

19. The method of claim 17, wherein the removing of the poly(vinylpyrrolidone) composition includes pushing it out by replacing it with a linear polyacrylamide.

20. A miniaturized apparatus for electrophoretic separations of solutes, the miniature apparatus prepared in accordance with a method comprising the steps of:

(a) providing, a substrate having a plurality of microchannels defined by the substrate;
(b) ailing the microchannels with a polyactam composition;
(c) adsorbing polyactam from the composition onto the internal surface of the microchannels, wherein the adsorbed amount of polyactam is sufficient to reduce electroosmotic flow during the subsequent use of the miniaturized apparatus in electrophoresis; and
(d) removing the polyactam composition from the microchannels while leaving adsorbed polyactam.

21. The miniaturized apparatus of claim 20, wherein polyactam is poly(vinylpyrrolidone).

22. The miniaturized apparatus of claim 21, wherein the composition comprises at least about 12% w/v poly (vinylpyrrolidone).

23. The miniaturized apparatus of claim 20, wherein the removing of the poly(vinylpyrrolidone) composition includes pushing it out by replacing it with a linear polyacrylamide.

* * * * *